United States Patent [19]

Bates et al.

[11] 4,273,012
[45] Jun. 16, 1981

[54] FOAM SPECIMEN APPARATUS AND METHOD

[75] Inventors: Edson C. Bates, Toledo, Ohio; Jeanne A. King, Huntington, N.Y.

[73] Assignee: Owens-Illinois, Inc., Toledo, Ohio

[21] Appl. No.: 109,946

[22] Filed: Jan. 7, 1980

[51] Int. Cl.³ .......................... B26D 4/50; B26D 7/08
[52] U.S. Cl. ........................................... 83/17; 83/42; 269/60
[58] Field of Search ................. 83/17, 42; 269/60, 71

[56] References Cited

U.S. PATENT DOCUMENTS

| 3,325,162 | 6/1967 | Lukas | 269/60 |
| 3,965,573 | 6/1976 | Mims | 269/60 X |

*Primary Examiner*—Frank T. Yost
*Attorney, Agent, or Firm*—David R. Birchall; Myron E. Click; David H. Wilson

[57] ABSTRACT

A device for aiding in the preparation of very thin slices of foam sheet material that is to be examined under a microscope. The device has a clamp arrangement for holding a sample of foam sheet material. A screw feed arrangement permits the foam sheet material to be advanced past a planar surface where a very thin slice of foam material can be removed. A clamping arrangement keeps the foam sheet material in linear alignment at the location where the sample is severed. A detent arrangement permits a metered amount of foam sheet material to be advanced past the planar cutting surface by the screw feed arrangement.

The method of preparing a foam sample by first severing the foam material while it is held by the apparatus, thus establishing a planar cut, then positioning the material for a second cut which is then made parallel to the first cut.

10 Claims, 2 Drawing Figures

FOAM SPECIMEN APPARATUS AND METHOD

BACKGROUND OF THE INVENTION

The present invention relates to the manufacture of foam sheet stock used in a wide variety of applications, such as for example containers, meat trays, packaging materials and antifriction place mats for airlines food service.

During the manufacture of foam sheet stock from materials such as polystyrene, polyethylene and the like, it is well known to introduce the basic polymer or copolymers into one or more extrusion devices in order to heat the polymer and incorporate therein certain nucleating agents, as well as the blowing agent. The thoroughly heated and masticated plastic material is then extruded through an extrusion orifice into a thin sheet or preferably a tube. When the extrudate takes the shape of a tube, it is drawn over a mandrel, thus expanding the circumferential extent of the tube. In addition, the tube of foam material is pulled away from the mandrel at a speed greater than the extrusion speed, thus inducing a certain amount of orientation into the foam sheet material. The orientation in a cellular foam sheet is a desirable feature in that certain memory characteristics can be built into the foam sheet. For example, it is now common to sever rectangular shaped pieces of foam sheet material and form them into cylinders having an overlapped liquid impervious seam. The cylinder thus formed is placed on a mandrel and subjected to controlled heat, thus causing the foam material to shrink and assume the configuration of the mandrel. Both one and two-piece drinking cups have been manufactured in this manner. Then too, a protective cover for bottles has been used for several years in the carbonated beverage field.

In order to monitor newly created foam sheet material, it is highly desirable to be able to examine in minute detail the actual cell structure within the sheet. Microscopic examination at, for instance, 60X magnification reveals several important aspects of how well the foam sheet has been fabricated. For example, it is highly important that the individual cells be of closed configuration if the ultimate purpose of the sheet material is for the fabrication of containers such as coffee cups and the like. A close-up examination of the cells within the sheet material reveals how well the surfaces of the foam material have been cooled. If the cooling is too rapid, small cell sizes will be created, thus acting as a bar to adequate cooling of the cells situated in the center of the sheet. Cells that receive inadequate cooling will have a tendency to rupture, thus reducing the overall integrity and usefulness of the sheet material. A good microscopic examination will reveal whether there has been an overload of the blowing agent and in the instance of a laminate, the skin thickness and uniformity can be monitored. A microscopic examination also permits an insight into the physical dimensions of each cell within the foam structure and its relationship with adjacent cells. As a foam material is generated soon after extrusion, the cells are normally spherical in configuration. With the introduction of orientation into the foam material, the originally spherical cells assume an elongate shape which they retain until subsequently released by the application of heat. Thus it becomes evident for several reasons to rely upon good microscopic examination of the individual cell structure in foam sheet material to assure adequate quality control.

SUMMARY OF THE INVENTION

The present invention relates to an apparatus for the preparation of foam sheet samples for microscopic examination. More particularly, the invention relates to an apparatus that permits a precisely measured laboratory foam sheet cross-sectional specimen to be prepared.

Foam sheet stock suitable for the manufacture of containers such as coffee and soft drink cups has an overall thickness in the range of 0.015 inch to 0.040 inch and a density of 10–15 pounds per cubic foot. Consequently, it is difficult to sever a thin parallel sided strip of foam sheet so that its edge structure can be examined microscopically. To cut such samples by the use of tools, such as scissors, would crush the delicate cell structure to such an extent that a detailed examination of the exposed sheet edge would not be meaningful. Thus it becomes imperative that the foam sheet samples be severed by means of a thin cutting blade such as a razor blade.

With this in mind it is one of the objects of the present invention to provide an apparatus that will grasp a foam sheet sample and permit a series of very linearly oriented parallel cuts to be made thereon.

The present apparatus includes a base structure for stabilization of the device and a clamping arrangement to grasp the foam sheet specimen without damaging it to the extent samples cannot be severed therefrom. The foam sheet can be advanced through the apparatus a prescribed amount and a planar surface is provided for the interaction with a cutting knife. Since the apparatus employs a screw thread specimen advance mechanism, it is possible to prepare repetitive samples, each having a uniform thickness with very parallel cut edges exposed for microscopic examination.

DESCRIPTION OF THE PREFERRED EMBODIMENT

Figures 1, 2:
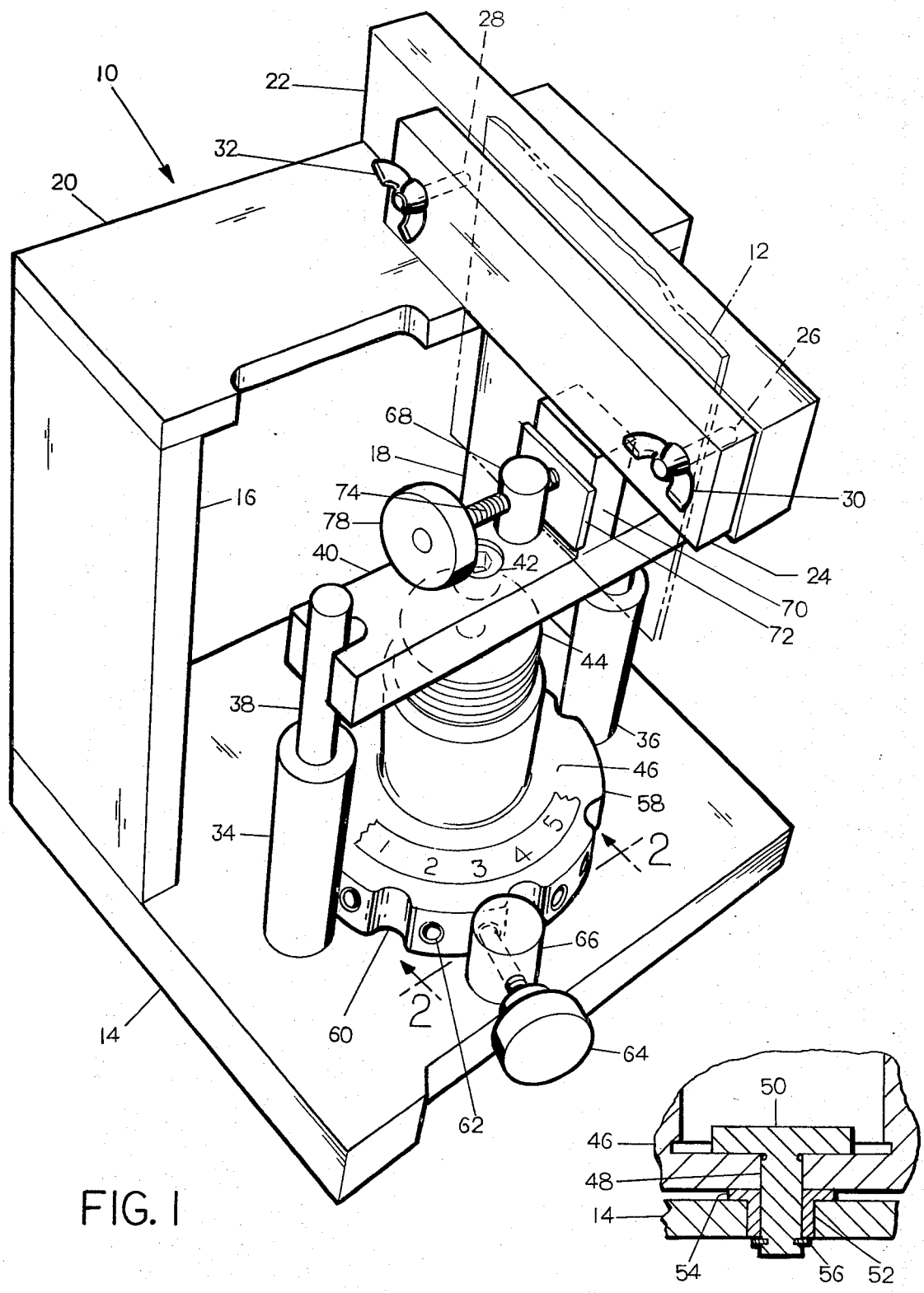
FIG. 1 is a perspective view of the sample preparation apparatus of the present invention.
FIG. 2 is a fragmentary sectional view, taken along lines 2—2 of FIG. 1 which shows the bottom tie-down connection for the hand nut.

The apparatus of the present invention is shown in FIG. 1. The overall apparatus is represented by numeral 10. The apparatus 10 represents a compact device for manipulating a foam sheet sample such as that depicted at 12. The foam sample 12 is prepared for use with apparatus 10 by first cutting it to a rectangular configuration.

In particular, apparatus 10 is supported by a base plate 14. Base plate 14 is generally rectangular in shape and is preferably constructed of metal. Two upright support columns 16 and 18 are attached to the top planar surface of base plate 14. The tops of support columns 16 and 18 are tied together by means of top deck plate 20. A support bar 22 is attached to the top surface of top deck plate 20 and is cantilevered so that it extends in a horizontal direction over the base plate 14. A clamp bar 24 is positioned adjacent one side of support bar 22 and is held in aligned engagement with support bar 22 by means of the threaded studs 26 and 28 which are anchored in support bar 22. Wing nuts 30 and 32 which coact with studs 26 and 28 provide a means for moving clamp bar 24 against support bar 22. The manner of use and function of the clamp bar 24 positioning and its use will be explained in more fully infra.

Returning once again to base plate 14, vertically aligned posts 34 and 36 are oriented to one another in spaced apart parallel positioning which is also perpendicular to base plate 14. Posts 34 and 36 are attached to the top of base plate 14 by conventional means (not shown). The top section 38 of posts 34 and 36 are of reduced diameter and coact with the bifurcated ends of saddle bar 40. Thus, as shown in FIG. 1, the saddle bar 40 is restrained from rotation by the engagement provided by posts 34 and 36. However, saddle bar 40 has freedom of movement in a vertical direction. Saddle bar 40 is rigidly attached, by a fastener such as bolt 42, to the top surface of threaded member 44. Threaded member 44 is of cylindrical configuration and is threaded with a low pitch thread on its exterior. An internally threaded hand nut 46 contains a centrally positioned internal bore that is threaded to match the threads on threaded member 44. Hand nut 46 is adapted for rotation both clockwise and counterclockwise and is rotatably anchored to base plate 14.

FIG. 2 which is a fragmentary cross-sectional view, further shows how hand nut 46 is attached to the top of base plate 14. An aperture 48 is placed in the bottom center of hand nut 46. A pivot pin 50 is passed through aperture 48, as well as a similar diameter aperture in bushing 52. Bushing 52 is pressed into an accommodating hole in base plate 14. The bushing 52 contains a flange 54 that provides sufficient space between the bottom of hand nut 46 and the top of base plate 14 so that there is no interference as hand nut 46 is rotated. The lower end of pivot pin 50 is grooved for the reception of a retaining ring 56 as shown in FIG. 2. Since hand nut 46 is held captive by means of pivot pin 50, its movement in the vertical direction is zero. However, when hand nut 46 is rotated, threaded member 44 will move in an upward or downward direction depending upon which direction hand nut 46 is rotated. Hand nut 46 has a large diameter flange-like disc 58 incorporated as an integral part of its lower extremity. Disc 58 is of sufficient overall diameter and thickness that it can be easily manipulated by hand. To further aid in the rotation of disc 58, notches 60 are positioned in a circumferentially spaced array around the periphery of disc 58. Interdispersed between notches 60 are bushings 62 which are carefully laid out so that the circumferential spacing therebetween is in equal increments. Each bushing 62 is in radial alignment with respect to the axis of rotation of hand nut 46. A detent mechanism 64 is positioned outboard of hand nut 46 and in radial alignment with the rotational axis of hand nut 46. The leading edge of detent mechanism 64 is adapted to enter bushings 62, thus securing hand nut 46 from rotation so long as the detent is engaged. The detent mechanism 64 is spring biased (not shown) and is operated by applying a radially outward force to the handle. The detent mechanism 64 is held in position by post 66 which is fastened to base plate 14.

Directing our attention once again to saddle bar 40, which is affixed to the top of threaded member 44, a lower clamp mechanism 68 is mounted on the top of saddle bar 40. The lower clamp mechanism 68 is positioned beneath the upper support bar 22. A clamp block 70 is attached to saddle bar 40 and its inboard face is in vertical alignment with the inboard face of support bar 22. A movable clamp pad 72 is positioned so that it will coact with clamp block 70. The clamp block 70 is attached to the end of screw 74. The attachment of screw 74 to clamp block 70 permits screw 74 to rotate without clamp block 70 also rotating. Screw 70 is held in position and in threaded engagement with support post 68. A convenient handle 78 is attached to screw 74 to facilitate the movement of clamp pad 72 into and out of clamping engagement with clamp block 70.

During the operation of overall apparatus 10, a foam sample, such as that depicted at 12, is sheared to a rectangular size that will permit it to be inserted in the expanse between studs 26 and 28 of support bar 22. The foam sample 12 is accommodated in the space between support bar 22 and clamp bar 24 and is lowered until its bottom edge rests firmly against the top surface of saddle bar 40. The foam sample 12 also passes between the gripping surfaces of clamp block 70 and coacting clamp pad 72. After the foam sample 12 has been positioned as described abovee, the lower clamp pad is moved into firm engagement with foam sample 12, thus clamping it into an immobile position with respect to saddle bar 40. The top clamp bar 24 is moved into engagement with foam sample 12, however, care is taken to only exert enough force to remove the slight curl which is inherent in foam sheet stock samples. This force is achieved by slowly tightening wing nuts 30 and 32 so that clamp bar 24 maintains its parallel orientation with respect to support bar 22. Thus when clamp bar 24 is in final position, it will have removed the curvature or curl from foam sample 12, yet it will not impede the free movement of foam sample in the vertical direction. At this point in the test procedure and sample preparation, it is desirable to permit an excess of foam sheet 12 to protrude above the top surfaces of support bar 22 and clamp bar 24. The hand nut 46 can, for example, be placed at stop position number 1 by removing detent mechanism 64 and reinserting it in the bushing 62 corresponding to position number 1 when the overall apparatus 10 and its included foam sample are in a position thus described above. A sharp instrument, such as a razor blade, is used to cut and remove that portion of foam sample 12 that protrudes above the surfaces of support bar 22 and coacting clamp bar 24. To assure an even cut across the expanse of foam sample 12, the cutting edge of the razor blade is held against the surfaces of support bar 22 and clamp bar 24. The just mentioned surfaces are at the same elevation, thus assuring that the newly cut surface of foam sample 12 is perpendicular to its planar side surfaces.

The hand nut 46 is freed from its locked position by retracting detent mechanism 64. Hand nut 46 is repositioned at stop position number 2. The slight turn of hand nut 46 from stop position 1 to stop position 2 results in the raising of foam sample 12 by 0.004 inch. This specific increment in the raising of the top edge of foam sample 12 above the top surfaces of support bar 22 and clamp bar 24 is achieved because of the following arrangement. The 0.004 inch rise of saddle bar 40 and its attached foam sample 12 is attributable to the laying out of the center lines of bushings 62 at angles of 25.714 degrees which results from 360 degrees divided by 14 equal stop positions. The thread employed on threaded member 44 is an 18 pitch thread, thus one revolution divided by $14 \times 18$ equals 0.00396 inch or when rounding off, 0.004 inch.

After hand nut 46 has been advanced to stop position 2, the razor blade is once again utilized to sever a 0.004 inch thick slice of foam material from the top edge of foam sample 12. The 0.004 inch sample is then carefully removed and mounted on double sticky back tape on a microscope slide.

If foam samples of greater thickness are desired, hand nut 46 is advanced more than one stop, thus resulting in sample thicknesses which are multiples of 0.004 inch.

Thus the present invention provides samples for another physical test in addition to other tests such as tensile, stretch, elongation, solvent resistance and surface cell size. The present invention permits test samples to be prepared which is an aid to establish performance criteria, for example, two foam materials may appear equal in physical tests, as well as in residual blowing agents, yet one foam material may be brittle and the other flexible or two different foam materials of the same caliper and density may vary as to their respective insulative qualities. An insight as to the differences between such foam materials can be gained by examining the precisely cut foam samples as prepared by the present invention.

Then too, the method provided by the present invention provides for the severing of foam test samples that have at least two cut sides that are parallel to one another. The present method preserves the structure of the individual cells within the sample so that the cells may be examined without undue distortion or mutilation occurring because of the sample preparation. The precise parallel orientation of the cut surfaces of the foam samples permits even transmission of light through the specimen during its microscopic examination.

What is claimed is:

1. A device for holding foam sheet material while samples are severed therefrom, including a base structure with an upright support frame attached thereto, a combination sheet guiding and cutting guide means cantilevered from said upright support frame, a foam sheet clamp means positioned beneath said guiding and cutting surface means, a screw advance means attached to said clamp means and to said base structure.

2. A foam sample holding device for aiding in the severing of thin strips of foam including a base structure for supporting the device, at least one upright column attached to said base structure, a support plate connected to the upper extent of said column, a combination sheet guiding and cutting guide means attached to and cantilevered from said support plate, a foam sheet clamp means positioned beneath said guiding and cutting surface means, said clamp means positioned on the top surface of a movable bar that is attached to a centrally positioned threaded member of a screw advance means which is pivotably attached to said base structure.

3. A device for holding foam sheet material while samples are severed therefrom including a base structure for supporting the device on a relatively planar horizontal surface, a plurality of upright columns attached to said base structure, a support plate connected to the upper extent of said columns, a combination sheet guiding and cutting guide means attached to and cantilevered from said support plate, said guide means being essentially planar on its top surface to facilitate the drawing of a knife blade thereover, a foam sheet clamp means positioned beneath and in alignment with said sheet guiding and cutting guide means, said clamp means positioned on a movable bar that is attached to a centrally positioned threaded member of a screw advance means, said movable bar coacting with guide posts positioned at each end of said bar, said screw advance means pivotally connected to said base plate structure.

4. A device as claimed in claim 3 wherein said sheet guiding and cutting means is comprised of a stationary bar and a movable bar coupled together by adjustment means so as to permit a flexible sheet of foam material to be clamped therebetween.

5. A device as claimed in claim 3 wherein said clamp means is comprised of a rigid clamp block and a movable clamp pad so as to permit a flexible sheet of foam material to be clamped therebetween.

6. A device as claimed in claim 3 wherein said screw advance means comprises a hand actuated nut with an internally threaded bore for reception of said centrally positioned threaded member, said nut containing a flanged section positioned adjacent said base structure and containing a plurality of circumferentially spaced apart radially aligned apertures.

7. A device as claimed in claim 6 wherein detent means is positioned on said base structure and coacts with the apertures in said flanged section.

8. A device as claimed in claim 6 wherein reentrant notches are positioned adjacent and between said apertures.

9. The method of preparing foam sheet samples for microscopic inspection including the steps of;
   (a) grasping one end of a foam sheet stock sample and fixing its position with respect to a first clamp means,
   (b) guiding the opposite end of said sample with a second clamp means so that said sample can move therethrough,
   (c) moving said first and second clamp means relative to one another so that said sample protrudes beyond a cutting surface on said first clamp means,
   (d) severing that portion of the foam sample that protrudes beyond said cutting surface.

10. The method of preparing foam sheet samples for microscopic inspection including the steps of;
   (a) severing a sample of foam sheet material from a larger sheet,
   (b) grasping one end of said sample with first clamp means so that the position of said sample is fixed with respect to said first clamp means,
   (c) grasping the opposite end of said sample with second clamp means so that the position of said sample is movable with respect to said second clamp means,
   (d) moving said first and second clamp means relative to one another so that said sample protrudes beyond a cutting surface on said first clamp means,
   (e) severing that portion of the foam sample that protrudes beyond said cutting surface,
   (f) advancing said second clamp means toward said first clamp means so that a prescribed amount of said sample protrudes beyond said cutting surface,
   (g) severing the prescribed amount of said sample so that it can be mounted for microscopic examination.

* * * * *